United States Patent [19]
Simmons

[11] Patent Number: 5,145,663
[45] Date of Patent: Sep. 8, 1992

[54] BIODEGRADABLE DISINFECTANT CONTAINING ANHYDROUS ALCOHOL AND PROPYLENE GLYCOL

[76] Inventor: Paul L. Simmons, 17819 Simmons Rd., Lutz, Fla. 33549

[21] Appl. No.: 642,709

[22] Filed: Jan. 17, 1991

Related U.S. Application Data

[63] Continuation of Ser. No. 304,312, Jan. 31, 1989, abandoned.

[51] Int. Cl.$^5$ .................... A61L 2/18; A61L 9/14; A61K 31/045; A61K 9/12
[52] U.S. Cl. ........................ 424/47; 424/45; 424/76.8; 514/975; 422/28
[58] Field of Search ................ 424/76.2, 76.8, 45, 424/47, 76.1

[56] References Cited

U.S. PATENT DOCUMENTS

| | | | |
|---|---|---|---|
| 580,213 | 4/1897 | Hakansson | 112/27 |
| 3,445,564 | 5/1969 | Kirschner | 424/45 |
| 3,806,593 | 4/1974 | Swanbeck et al. | 424/401 |
| 3,821,413 | 6/1974 | Hellyer, Jr. | 424/76.2 |
| 4,072,742 | 2/1978 | Bouillon et al. | 424/47 |
| 4,336,270 | 6/1982 | Muntwyler | 424/47 X |
| 4,511,486 | 4/1985 | Shah | 424/45 |
| 4,664,909 | 5/1987 | Marschner | 424/69 |
| 4,678,658 | 7/1987 | Casey et al. | 424/43 |
| 4,690,779 | 9/1987 | Baker et al. | 252/546 |

*Primary Examiner*—Thurman K. Page
*Assistant Examiner*—E. J. Webman
*Attorney, Agent, or Firm*—Arthur W. Fisher, III

[57] ABSTRACT

A non-toxic, non-corrosive, biodegradable disinfectant for use against various pathogenic organisms comprising a homogeneous composition of interactive constituents including anhydrous alcohol, in particular, isopropyl alcohol, propylene glycol, maskant and inert ingredients wherein the propylene glycol reduces the surface glaze formed by the anhydrous alcohol and surface tension formed by water or water-based body fluids enabling the disinfectant to rapidly contact the pathogenic organisms.

7 Claims, No Drawings

BIODEGRADABLE DISINFECTANT CONTAINING ANHYDROUS ALCOHOL AND PROPYLENE GLYCOL

CO-PENDING APPLICATION

This application is a continuation application of pending application Ser. No. 304,312, filed Jan. 31, 1989 now abandoned.

BACKGROUND OF THE INVENTION

1. Field of the Invention

A non-toxic, non-corrosive, biodegradable disinfectant effective against various pathogenic organisms.

2. Description of the Prior Art

Rapid increases in the spread of deadly communicable diseases such as AIDS virus (HIV) have dramatically escalated public awareness for the need of an effective protective means.

The need for such protective means applies equally to contaminated surfaces such as those found in public restrooms, telephones, tables and other surfaces contacted by the public as well as for topical application directly on a patient's skin.

A common means for such surface protection is typified by a disposable paper cover for a toilet. Such disposable paper covers often do not contain a germicide and are not always available or easily used.

Various spray germicides for sanitizing such surfaces is typified by in U.S. Pat. No. 3,445,564. In addition, the use of a dye in a bacteracidal solution as disclosed in U.S. Pat. No. 2,449,274 is employed to provide a visual indication of the effectiveness of such sprays.

U.S. Pat. No. 4,678,658 shows disinfecting compounds effective as germicides reducing surface tension to more effectively distribute the germicide spray on the surface. However, the spray is corrosive and environmentally unsafe.

U.S. Pat. No. 3,821,413 teaches a disinfectant consisting of propylene glycol to stabilize the composition and retard evaporation. This disinfectant is toxic, corrosive and non-biodegradable.

U.S. Pat. No. 3,966,902 disclosed various polymer complex carriers such as propylene glycol for use with an active ingredient such as a disinfectant or fragrance.

U.S. Pat. No. 4,690,779 refers to the use of propylene glycol in combination with alcohol and fragrances. This composition is both toxic and non-biodegradable.

U.S. Pat. No. 4,209,500 teaches a composition suitable for use in aerosol sprays including an anhydrous alcohol and fragrance or perfume. This composition is corrosive, non-biodegradable and non-evaporative.

Additional examples of the prior art are found in U.S. Pat. No. 580,213, U.S. Pat. No. 4,282,179, U.S. Pat. No. 4,265,899, U.S. Pat. No. 4,283,421, U.S. Pat. No. 4,364,515, U.S. Pat. No. 4,550,105, U.S. Pat. No. 4,105,431, U.S. Pat. No. 4,243,403, U.S. Pat. No. 4,278,206, U.S. Pat. No. 4,322,475, U.S. Pat. No. 4,436,732, U.S. Pat. No. 4,597,887, U.S. Pat. No. 4,252,694, U.S. Pat. No. 4,279,762, U.S. Pat. No. 4,325,201, U.S. Pat. No. 4,540,505 and U.S. Pat. No. 4,675,397.

Examination of the prior art fails to teach or suggest an effective surface active disinfectant for application on contaminated surfaces or a patient's skin through a spray or liquid application.

SUMMARY OF THE INVENTION

The present invention relates to a non-toxic, non-corrosive, biodegradable disinfectant for topical application on a patient's skin or to surfaces to kill various pathogenic organisms.

The non-toxic, non-corrosive, biodegradable disinfectant comprises a composition of interactive constituents including anhydrous alcohol, propylene glycol and inert ingredients combined in specific relative proportions by weight such that the non-toxic, non-corrosive, biodegradable disinfectant may be used safely to disinfect a patient's skin through topically application or to disinfect various surfaces with equal disinfecting effectiveness. The interactive composition comprises anhydrous alcohol 70%, propylene glycol 10%, fragrance 1% and inert ingredients 19% by weight.

The anhydrous alcohol provides the primary disinfecting or killing effect on the pathogenic organisms. The propylene glycol lowers the flash point of the disinfectant and soothes the skin. The propylene glycol also slows the rate of evaporation, reduces or eliminates the intersurface glazing effect of anhydrous alcohol and homogenizes the interactive ingredients.

The critical balance of interactive ingredients chemically reduces the tensile strength of the surface liquids on the patient's skin or other surface permitting the disinfecting effect to act directly on the pathogenic organisms.

The invention accordingly comprises the features of construction, combination of elements, and arrangement of parts which will be exemplified in the construction hereinafter set forth, and the scope of the invention will be indicated in the claims.

DETAILED DESCRIPTION OF THE PREFERRED EMBODIMENT

Various compositions and devices have been developed to disinfect various pathogenic organisms. Catholic application is limited by the chemical and biological effect of such compositions or limitations on various surfaces, delivery means and patients.

The present invention relates to a non-toxic, non-corrosive, biodegradable disinfectant and antiseptic for topical application on a patient's skin or on hard surfaces such as restrooms or tables against various pathogenic organisms such as bacteria including *Staphylococcus aureus, Pseudomonas aeruginosa* and *Salmonella coleraesuis* and viruses, including HIV-I, HIV-II and herpes simplex type 2 as well as fungi, mold and mildew through numerous delivery means.

The non-toxic, non-corrosive, biodegradable disinfectant of the subject invention comprises an interactive composition of anhydrous alcohol, propylene glycol and inert ingredients combined in specific relative proportions by weight such that the disinfectant may be used topically to disinfect a patient's skin or to disinfect various public surfaces through direct application with equal effectiveness.

This unique disinfectant is effective against various pathogenic organisms common to the general environment without deleterious non-toxic effect on patients or damage to surfaces or dispensing devices as exemplified herein. The optimum proportional relationship of the ingredients by weight is anhydrous alcohol 70%, propylene glycol 10%, fragrance 1% and inert ingredients 19%.

The anhydrous alcohol is effective in a 65 to 75 percent range.

The effective range of propylene glycol is between 8 to 12 percent by weight. This proportion is critical to the universal use of the instant disinfectant. During development of the instant invention numerous concentrations were tested. The optimum proportions provide a disinfectant effective against numerous pathogenic organisms without harming or destroying the dispensing means, disinfected surface or patient.

The optimum percentage of propylene glycol raises the boiling point of the disinfectant slowing the rate of evaporation. As a solvent the propylene glycol prevents the tendency of isopropanol to form a glaze on the target surface that masks the pathogenic organisms and breaks the barrier formed by surface tension of water and water-based body fluids enabling the disinfectant to act on the virus or organism more rapidly. The effectiveness is reduced to a one minute kill label claim, rather than ten minutes as in most other disinfectants. In addition the proplene glycol serves as an emulsifier to assure that the fragrance and alcohol remain homogenized during storage and use.

Further the propylene glycol reduces the harmful effects of alcohol if swallowed or sprayed into the eye or on mucus membranes as well as soothing the skin upon contact. Since the propylene glycol reduces toxicity to human cells the need to dilute the disinfectant has been eliminated. Propylene glycol also acts as a secondary disinfectant useful to disinfect air. In the preferred percentage used tests indicate that the propylene glycol increases the overall effectiveness against most viruses, mold and mildew.

Since the disinfectant was developed for use on a wide variety of surfaces and dispensed from a number of dispensing modes or means of dispersant materials the measure of chemical resistance is important to provide universal use and application. As shown by the following chemical resistance chart the present invention compares favorably to propylene glycol and isopropyl alcohol.

| Material | Propylene Glycol | Isopropyl Alcohol | Disinfectant |
|---|---|---|---|
| CPVC | C1 | A2 | B2 |
| Epoxy | C | A | B |
| Polypropylene | B2 | A2 | A2 |
| PVC | C1 | B1 | A1 |
| Cyolac (ABS) | B | — | B |
| Phenolic | A | A | A |
| Nylon | — | B1 | B1 |
| Noryl | — | A1 | A1 |
| Delrin (Acetal) | B | A | A |
| Ryton to 200° F. | — | — | — |
| Kynar (PVDF) | — | — | — |
| Teflon | A | A2 | A2 |
| Stainless Steel 316 | B | A | A |
| Stainless Steel 304 | B | A | A |
| Carpenter 20 | A | A | A |
| Stainless steel (440) | — | — | — |
| Titanium | A | A | A |
| Cast Bronze | A | A | A |
| Cast Iron | A | C | B |
| Aluminum | B | B | B |
| Hastelloy C | B | B | B |
| Carbon/ceramic | A | A | A |
| Ceramagnet A | — | — | — |
| Viton | A | A | A |
| Buna N. | A | B | A |
| Neoprene | C | B | B |
| Nitrile | A | B | A |
| Natural rubber | — | A | A |
| Hypalon | — | A | A |
| EPDM | — | A | A |
| Kel-F | — | — | — |
| Tygon | — | — | — |
| Silicone | — | A | A |
| Ceramic | A | A | A |
| Carbon/graphite | — | A | A |

The following legend is provided to interpret the foregoing chart.

| Ratings-chemical effect | Explanation of footnotes |
|---|---|
| A-No effect-Excellent | 1 Satisfactory to 72° F. |
| B-Minor effect-Good | 2 Satisfactory to 120° F. |
| C-Moderate effect-Fair | 3 Satisfactory for O-rings |
| D-Severe effect-Not recommended | |

An examination of this chart and the comparative results clearly demonstrates that the optimum combination of interactive ingredients of the instant invention provides a disinfective effective against an expansive range of materials found in a wide variety environments through various delivery means such as aerosol, pump, spray or swab.

The non-toxic, biodegradable aspect of the disinfectant permits disposal without polluting ground water.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A non-toxic, non-corrosive, biodegradable disinfectant and antiseptic for use against various pathogenic organisms, said disinfectant and antiseptic consisting essentially of about 65 to 75% by weight isopropyl alcohol and about 8 to 12% by weight propylene glycol, mixed homogeneously and performing interactively in a proportion by weight such that said propylene glycol reduces the surface glaze formed by said isopropyl alcohol and surface tension formed by water or water-based body fluids enabling said disinfectant to rapidly contact the pathogenic organisms and act equally effective on a patient or inanimate surface without deleterious effect.

2. A non-toxic, non-corrosive, biodegradable disinfectant and antiseptic according to claim 1, said isopropyl alcohol being present in an amount of about 70 percent by weight.

3. A non-toxic, non-corrosive, biodegradable disinfectant and antiseptic according to claim 2, at least about 19 percent by weight of said disinfectant and antiseptic being inert ingredients.

4. A non-toxic, non-corrosive, biodegradable disinfectant and antiseptic according to claim 1, wherein said propylene glycol is present in an amount of about 10 percent by weight.

5. A non-toxic, non-corrosive, biodegradable disinfectant and antiseptic according to claim 4, said isopropyl alcohol being present in an amount of about 70 percent by weight.

6. A non-toxic, non-corrosive, biodegradable disinfectant and antiseptic according to claim 5, at least about 19 percent by weight of said disinfectant and antiseptic being inert ingredients.

7. A non-toxic, non-corrosive, biodegradable disinfectant and antiseptic according to claim 1, at least about 19 percent by weight of said disinfectant and antiseptic being inert ingredients.

* * * * *